United States Patent
Noda

(10) Patent No.: US 10,362,938 B2
(45) Date of Patent: Jul. 30, 2019

(54) FUNDUS IMAGE FORMING DEVICE

(71) Applicant: NIKON CORPORATION, Minato-ku, Tokyo (JP)

(72) Inventor: Tomoya Noda, Saitama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/630,344

(22) Filed: Jun. 22, 2017

(65) Prior Publication Data

US 2017/0347882 A1 Dec. 7, 2017

Related U.S. Application Data

(63) Continuation of application No. PCT/JP2014/084619, filed on Dec. 26, 2014.

(51) Int. Cl.
*A61B 3/10* (2006.01)
*A61B 3/12* (2006.01)
(Continued)

(52) U.S. Cl.
CPC .................. *A61B 3/12* (2013.01); *A61B 3/10* (2013.01); *A61B 3/1025* (2013.01); *A61B 3/14* (2013.01); *G02B 17/06* (2013.01)

(58) Field of Classification Search
CPC ........... A61B 3/12; A61B 3/10; A61B 3/1025; A61B 3/14; G02B 17/06
(Continued)

(56) References Cited

U.S. PATENT DOCUMENTS 5,815,242 A 9/1998 Anderson et al.
7,959,290 B2 * 6/2011 Cairns .................. A61B 3/1225
351/206
(Continued)

FOREIGN PATENT DOCUMENTS

JP 2009-543585 A 12/2009
JP 2014-502552 A 2/2014
(Continued)

OTHER PUBLICATIONS

International Preliminary Report on Patentability and Written Opinion of the International Search Authority issued in application No. PCT/JP2014/084619 dated Jun. 27, 2017.
(Continued)

*Primary Examiner* — Collin X Beatty
(74) *Attorney, Agent, or Firm* — Foley & Lardner LLP

(57) ABSTRACT

A fundus imaging system comprises: a reflection mirror that reflects a light beam incident on the reflection mirror after passing through a first focus so as to cause the light beam to pass through a second focus; a two-dimensional scanning unit that is disposed at a position that coincides with a position of the first focus of the reflection mirror and that reflects a light beam incident on the two-dimensional scanning unit so as to perform scanning with the light beam in two-dimensional directions; and a compensating unit that compensates for illuminance ununiformity of a light beam illuminating the retina, the illuminance ununiformity resulting from unevenness of a ratio of an angular change of a light beam emitted from the first focus during scanning of the two-dimensional scanning unit to an angular change of a light beam incident on the second focus resulting from being reflected by the reflection mirror.

8 Claims, 4 Drawing Sheets

(51) Int. Cl.
*A61B 3/14* (2006.01)
*G02B 17/06* (2006.01)

(58) Field of Classification Search
USPC .......................................................... 351/206
See application file for complete search history.

(56) References Cited

U.S. PATENT DOCUMENTS

| | | | |
|---|---|---|---|
| 9,078,603 B2* | 7/2015 | Thomson | A61B 3/1025 |
| 2002/0036750 A1* | 3/2002 | Eberl | A61B 3/12 351/207 |
| 2010/0141895 A1 | 6/2010 | Cairns et al. | |
| 2010/0220287 A1* | 9/2010 | Sumiya | A61B 3/10 351/206 |
| 2012/0133888 A1 | 5/2012 | Gray et al. | |
| 2012/0188614 A1 | 7/2012 | Azegrouz | |
| 2012/0257166 A1 | 10/2012 | Francis et al. | |
| 2013/0093996 A1 | 4/2013 | Thomson et al. | |
| 2013/0135583 A1 | 5/2013 | Gray et al. | |
| 2013/0335703 A1 | 12/2013 | Creasey et al. | |
| 2014/0327882 A1 | 11/2014 | Muyo et al. | |
| 2018/0008141 A1* | 1/2018 | Krueger | G16H 50/30 |
| 2018/0064577 A1* | 3/2018 | Malek Tabrizi | A61B 3/1005 |

FOREIGN PATENT DOCUMENTS

| | | | |
|---|---|---|---|
| JP | 2014-068703 A | 4/2014 | |
| WO | WO 2012095620 A1 * | 7/2012 | A61B 3/0008 |

OTHER PUBLICATIONS

International Search Report issued in application No. PCT/JP2014/084619 dated Feb. 3, 2015.
Japanese Office Action and its English translation thereof issued in corresponding application No. 2016-565826 dated Apr. 3, 2018.
Chinese Office Action and its English translation thereof issued in corresponding application No. 201480084340.5 dated Apr. 25, 2018.
Extended European Search Report dated Jul. 9, 2018 received in corresponding European Application No. 14909087.0.
Japanese Office Action and its English translation thereof issued in corresponding Japanese Application No. 2016-565826 dated Oct. 23, 2018.

* cited by examiner

FUNDUS IMAGE FORMING DEVICE

BACKGROUND

1. Technical Field

The present invention relates to a fundus imaging system.

2. Related Art

Examples of a fundus scanning system that scans a retina of a subject include a system that: vertically scans the retina with a laser beam using a polygon mirror and concurrently causes the laser beam to be incident on a first elliptical mirror; horizontally scans the retina with a light beam reflected off the first elliptical mirror using an oscillating plane mirror and concurrently causes the light beam to be incident on a second elliptical mirror; and causes a light beam reflected off the second elliptical mirror to be incident on a pupil of the subject (see, for example, Patent Document 1).

Patent Document 1: Japanese Unexamined Patent Application Publication (Translation of PCT Application) No. 2009-543585

The above-described fundus scanning system, however, is disadvantageous in that the entire system is increased in size because it includes two large spherical mirrors, that is, a first elliptical mirror and a second elliptical mirror.

SUMMARY

According to a first aspect of the present invention, a fundus imaging system scanning a retina of a subject with a light beam, including: a reflection mirror that reflects a light beam incident on the reflection mirror after passing through a first focus so as to cause the light beam to pass through a second focus; a two-dimensional scanning unit that is disposed at a position that coincides with a position of the first focus of the reflection mirror and that reflects a light beam incident on the two-dimensional scanning unit so as to perform scanning with the light beam in two-dimensional directions; and a compensating unit that compensates for illuminance ununiformity of a light beam illuminating the retina, the illuminance ununiformity resulting from unevenness of a ratio of an angular change of a light beam emitted from the first focus during scanning of the two-dimensional scanning unit to an angular change of a light beam incident on the second focus as a result of being reflected by the reflection mirror.

The summary clause does not necessarily describe all necessary features of the embodiments of the present invention. The present invention may also be a sub-combination of the features described above.

DESCRIPTION OF EXEMPLARY EMBODIMENTS

Hereinafter, the present invention is described through the embodiments of the invention. However, the following embodiments do not limit the invention according to the scope of claim. Also, all the combinations of the features described in the embodiments are not necessarily essential to means provided by aspects of the invention.

Figure 1:
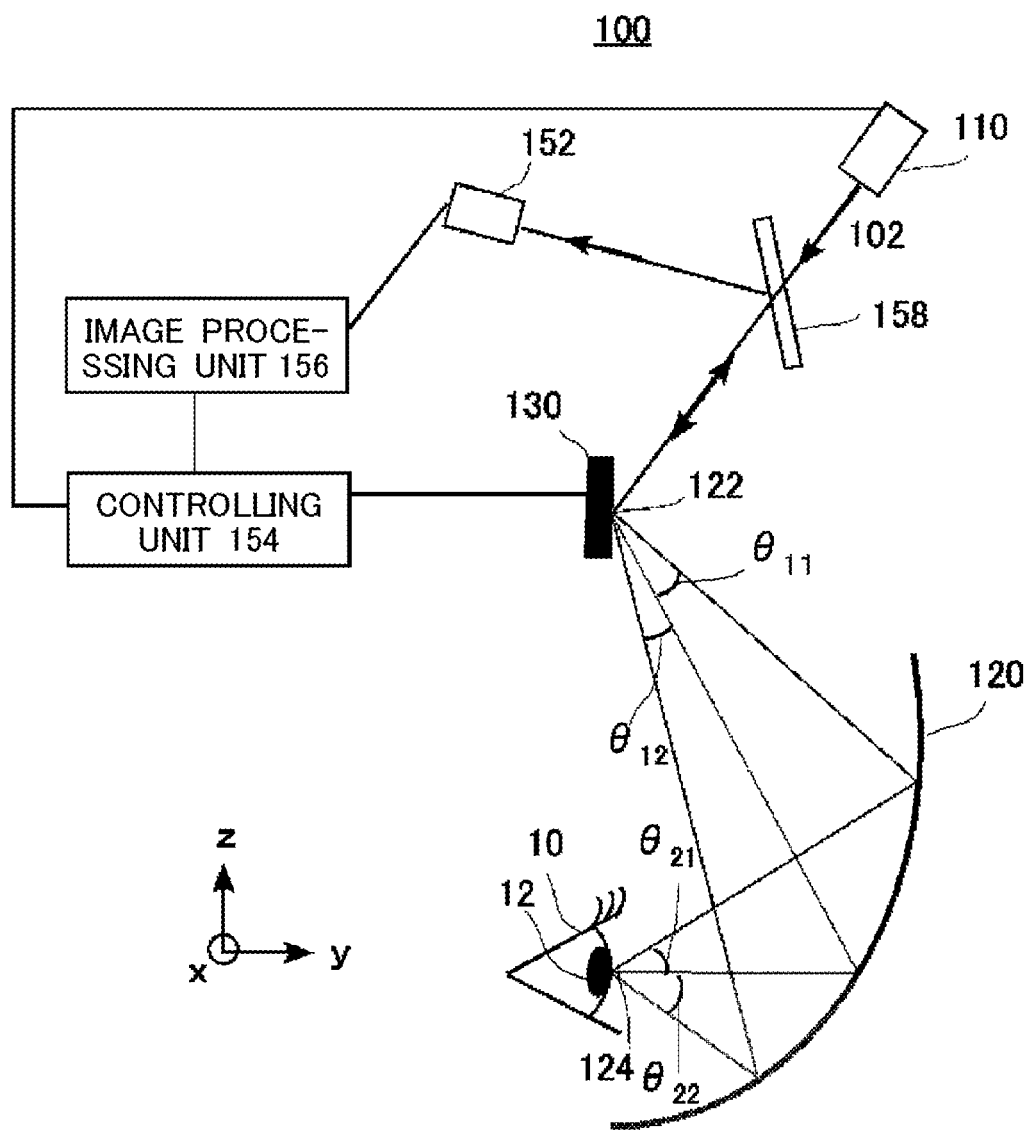
FIG. 1 is a schematic diagram of a fundus imaging system 100.

FIG. 1 is a schematic diagram of a fundus imaging system 100. The x, y and z directions are defined as shown in the figure. All of these are for description, and any of them may be in the vertical direction or in the horizontal direction.

The fundus imaging system 100 includes a light source 110, a half-silvered mirror 158, a two-dimensional scanning unit 130, a reflection mirror 120, a detector 152, a controlling unit 154, and an image processing unit 156.

The light source 110 emits a light beam 102 to illuminate an eye 10 of a subject. The wavelength of the light beam 102 may be selected according to a target of the imaging, and it is, for example, the infrared region wavelength, the visible light region wavelength, and the like. Although one light source 110 is shown in the example shown in FIG. 1, a plurality of light sources which emit light with different wavelengths may be used. When the plurality of light sources are used, light beams from respective light sources are placed on the same optical path by a beam combiner. Also, it is more preferable to use a laser light as the light beam because it has good linearity.

The half-silvered mirror 158 transmits and reflects the light beam 102 incident on the half-silvered mirror 158 at a ratio designed in advance. The half-silvered mirror 158 transmits the light beam 102 from the light source 110, and it reflects the light beam 102 returned from the eye 10 and leads the light beam to the detector 152.

The reflection mirror 120 has a first focus 122 and a second focus 124. The reflection mirror 120 reflects a light beam 102 incident on the reflection mirror 120 after passing through the first focus 122 so as to cause the light beam 102 to pass through the second focus 124. One example of the reflection mirror 120 is an elliptical reflection mirror which has a reflection surface formed by a part of a rotary ellipsoid obtained by rotating an ellipse around a major axis including the first focus 122 and the second focus 124.

The two-dimensional scanning unit 130 is disposed so as to coincide with the first focus 122 of the reflection mirror 120. About the positional relationship between the two-dimensional scanning unit 130 and the first focus 122 of the reflection mirror, there may be cases where the respective positions are actually coincident as shown in FIG. 1, or, where they are the same in design, but are inevitably misaligned due to assembling error, etc. Although it is preferable that these positions are ideally coincident respectively, coincidence of these positional relationships at a predetermined range is permitted. The range is a range that allows a scanning light beam to enter a pupil of an eye when the angle of the light beam is two-dimensionally scanned at an iris position of the eye 10 of the subject, and is a range that will not bring about obstacle to the fundus imaging.

And, in an actual application of the fundus imaging of the eye of the subject by this system, it is important to cause the pupil position of the eye 10 of the subject to coincide with the second focus 124 of the reflection mirror 120. By moving a member other than the reflection mirror 120 in response to a subtle position change of the eye 10, it is possible to cause the substantial center position of the angular scanning of the light beam to follow the position of the pupil of the eye 10. Among other things, it is effective to make the portions from light source 110 to the two-dimensional scanning unit 130 integrally movable and cause them to follow the position change of the eye of the subject.

Figure 2:
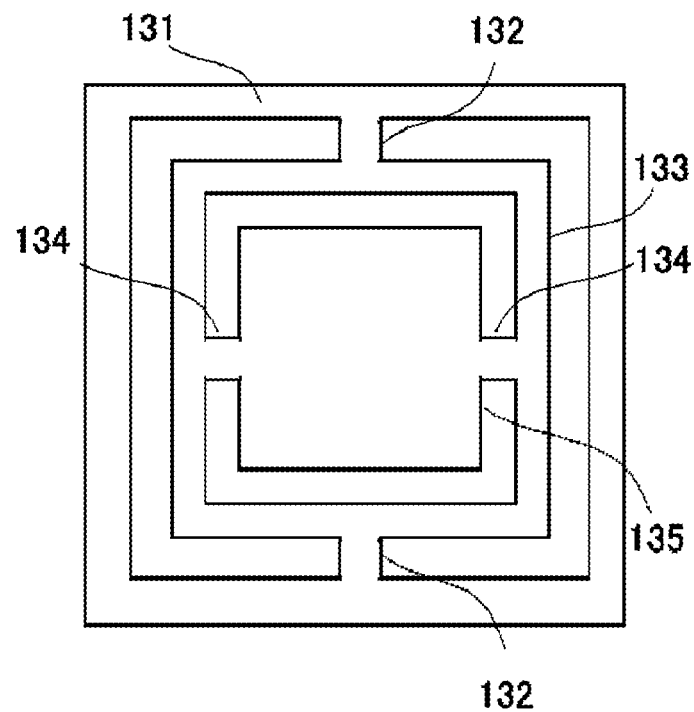
FIG. 2 is a schematic diagram of one example of a two-dimensional scanning unit 130.
Figure 2:
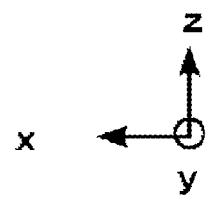

FIG. 2 is a schematic diagram of one example of the two-dimensional scanning unit 130. The two-dimensional scanning unit 130 has a body 131, a frame 133 which is supported by the junction 132 so as to be freely rotatable around the z axis relative to the body 131, and a reflection mirror 135 which is supported by the junction 134 so as to be freely rotatable around the x axis relative to the frame 133, and reflects the light beam 102. The two-dimensional scanning unit 130 has a so-called gimbal structure, and is configured with, for example, MEMS, and is, for example, electrostatically driven by the controlling unit 154.

In the above-described configuration, the pupil 12 of the subject is positioned within a predefined range relative to the second focus 124 of the reflection mirror 120. "A predefined range" meets a condition in that it is similar to the above-described positional relationship between the two-dimensional scanning unit 130 and the first focus 122 of the reflection mirror. The controlling unit 154 causes the light beam 102 to emit from the light source 110, and additionally by controlling a rotation amount of the two-dimensional scanning unit 130 to rotate the reflection mirror 135 around the z axis and around the x axis, the controlling unit 154 scans with the light beam 102 from the light source 110 in the z direction and the x direction.

The light beam 102 from the two-dimensional scanning unit 130 is reflected off the reflection mirror 120, passes through the pupil 12, and reaches the retina (not illustrated) of the eye of the subject 12. The light beam 102 reflected off the retina reversely traces the above-described optical path and reaches the half-silvered mirror 158. The light beam 102 reflected off the half-silvered mirror 158 is detected by the detector 152. Based on the rotation amount of the two-dimensional scanning unit 130 controlled by the controlling unit 154, and the light amount detected by the detector 152, the image processing unit 156 two-dimensionally reconfigures an image of the retina and outputs it to a monitor, etc.

Here, the relationship between the angular change of the light beam 102 that the two-dimensional scanning unit 130 causes to be emitted from the first focus 122, and the angular change of the light beam 102 that is reflected off the reflection mirror 120 to be incident on the second focus 124 is considered. For example, the case where the two-dimensional scanning unit 130 performs scanning with the light beam only by the angular change $\theta_{11}$ around the x axis from a certain angle, and the case where the two-dimensional scanning unit 130 scans with the light beam only by the same angular change $\theta_{12}$ (that is, $\theta_{11}=\theta_{12}$) further around the x axis, as shown in FIG. 1, are considered.

In the above-described scanning, a reflection portion of the reflection mirror 120 is scanned in a direction of an arrow A in the figure. Because curvatures of portions of the reflection mirror 120 differ respectively, the respective angular changes $\theta_{21}$, $\theta_{22}$ at which the reflected light beam heads to the second focus 124 relative to the same angular changes $\theta_{11}$, $\theta_{12}$ differ in general (that is, $\theta_{21} \neq \theta_{22}$). Although the angles can be geometrically calculated respectively, the angular changes are $\theta_{21} < \theta_{22}$ in the example in FIG. 1.

In other words, the ratio of the angular change of the light beam 102 which is emitted from the first focus 122 to the angular change of the light beam 102 which is reflected off the reflection mirror 120 to be incident on the second focus 124, corresponding to the angular change is not even ($\theta_{11}/\theta_{12} \neq \theta_{21}/\theta_{22}$).

Thus, if the two-dimensional scanning unit 130 performs scanning the above-described angular changes $\theta_{11}$, $\theta_{12}$ at a constant speed, the speed at which the two-dimensional scanning unit 130 scans the retina of the eye 10 after passing through the second focus 124 is different. In the above-described example, if $\theta_{21} < \theta_{22}$ when $\theta_{11}=\theta_{12}$, about the speeds of the scanning on the retina corresponding to the relationship, v1<v2 is satisfied. Here, if an intensity of the light beam 102 from the light source 110 is constant during the scanning, the faster the speed at which the retina is scanned, the smaller the time integral value of the light beam 102 which illuminate the retina is. In the above-described example, if the speed at which the scanning is performed satisfies v1<v2, the illuminance in the scan area on the respective retinas satisfies I1>I2. That is, this becomes unevenness in illumination of the retina.

Therefore, in the embodiment, the unevenness in illumination is compensated for. Here, in order to compensate for the unevenness in illumination, two methods are possible, which are a method of actually adjusting the intensity of the light beam 102, and a method of correcting the detection result after detection by the detector 152. In the embodiment, the controlling unit 154 corrects the detection result after detecting by the detector 152. In this respect, the controlling unit 154 serves concurrently as a compensating unit.

The controlling unit 154 corrects the result of the detection of the intensity of the light beam 102 by the detector 152 based on at least one of the scan angle and the scan timing at which the two-dimensional scanning unit 130 performs scanning. As described above, if a geometric parameter such as an eccentricity of the reflection mirror 120 and at least one of the scan angle or the scan timing at which the two-dimensional scanning unit 130 performs scanning are known, the illuminance ununiformity during scanning can be calculated. Thus, the controlling unit 154 corrects the result of the detection so as to compensate for the illuminance ununiformity, and passes it to the image processing unit 156. For example, if it is known that the illuminance satisfies I1>I2 relative to the angular changes of the scanning $\theta_{11}$, $\theta_{12}$, in the above-described example, the detection result of the angular change $\theta_{12}$ is multiplied by an amount of compensation $\alpha$ which is larger than one, and is compensated for so that I1=$\alpha$I2 is satisfied.

In this case, the controlling unit 154 may calculate the amount of compensation on a case-by-case basis according to the scan angle and the scan timing, or may store a table or the like in a memory of the controlling unit 154 or the like in advance. The table stores an amount of compensation of the illuminance ununiformity in association with at least one of the scan angle or the scan timing that are calculated based on the geometric parameter of the reflection mirror 120. In this case, the memory of the controlling unit 154 functions as a compensation amount storage unit. Instead of this, an amount of compensation corresponding to at least one of the scan angle and the scan timing may be set so as to measure a known brightness index such as a test chart, and so that its measurement result can reproduce the known brightness.

Figure 3:
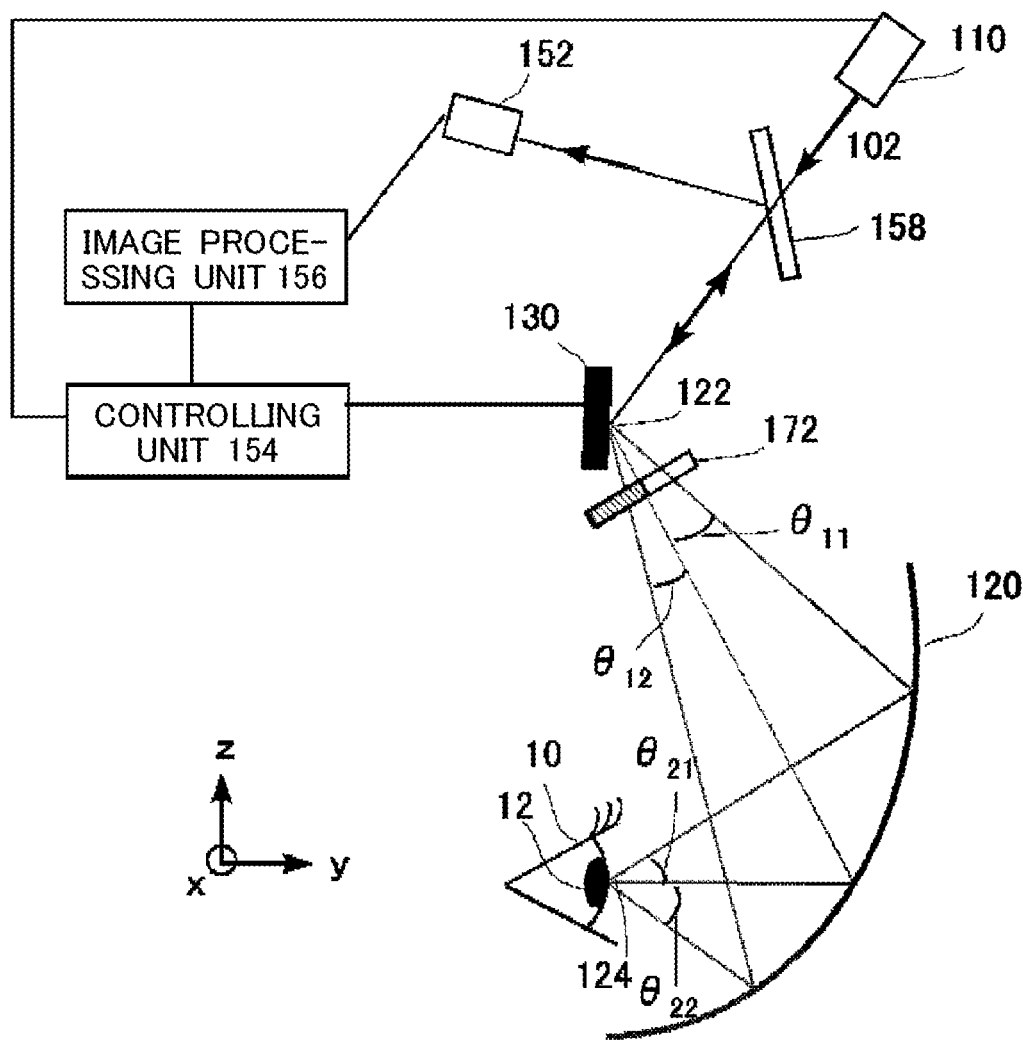
FIG. 3 is a schematic diagram of another fundus imaging system 170.

FIG. 3 is a schematic diagram of another fundus imaging system 170. In the fundus imaging system 170, the same configurations as the fundus imaging system 100 in FIG. 1 are given the same reference numbers, and a description about them will be omitted.

The fundus imaging system 170 has an intensity compensation optical system 172 in addition to the respective configurations of the fundus imaging system 100. The intensity compensation optical system 172 is disposed in the optical path of the light beam 102, and between the two-dimensional scanning unit 130 and the reflection mirror 120 in the example in FIG. 3.

The intensity compensation optical system 172 is, for example, a transmission plate in which transmittances are two-dimensionally distributed. The intensity compensation optical system 172 compensates for the above-described unevenness by two-dimensionally distributing the transmittance of the light beam 102 after being incident. In the above-described example of I1>I2, because the transmittance of the position at which the light beam of $\theta_{11}$ corresponding to the intensity I1 incident on the light beam is set to $1/\alpha$, $I1/\alpha=I2$ is satisfied, and the intensity distribution with the above-described unevenness compensated for is realized. Note that although in the figure, the transmittance changes stepwise for simplicity, it is preferable for the transmittance to change continuously.

In this way, the intensity compensation optical system 172 of the embodiment represents one example of a method which corrects the unevenness in illumination by actually adjusting the intensity of the light beam 102. In accordance with the embodiment, the illuminance ununiformity can be compensated for with simple and convenient configuration. Note that a reflection plate may be used instead of the transmission plate and the reflectance may be two-dimensionally distributed. Furthermore, instead of separately providing the intensity compensation optical system 172, by two-dimensionally distributing the reflectance on the reflection surface of the reflection mirror 120 by providing a coating and the like to the reflection surface of the reflection mirror 120, the above-described unevenness may be compensated for.

In such a configuration, the luminance difference due to the fundus oculi position of the scanning light sensed by the eye of the subject due to the illuminance ununiformity of the light beam 102 to the retina is corrected. The luminance results from the unevenness of a ratio of the angular change of the light beam 102 emitted from the first focus 122 by the scanning performed by the two-dimensional scanning unit 130 to the angular change of the light beam that is reflected off the reflection mirror 120 and is incident on the second focus. And a feeling of discomfort of the subject can be eliminated. On the other hand, the unevenness which occurs in the intensity detector 152 of the reflected light beam from the fundus oculi due to the illuminance ununiformity of the similar light beam can also be compensated for. In this case, because the light beam 102 passes through the intensity compensation optical system 172 twice when it heads to the fundus oculi and when it is reflected off the fundus oculi, it is necessary to cause the intensity compensation optical system 172 to have a different compensation function from that of when the beam intensity evenness in the eye of the subject is maintained.

Figure 4:
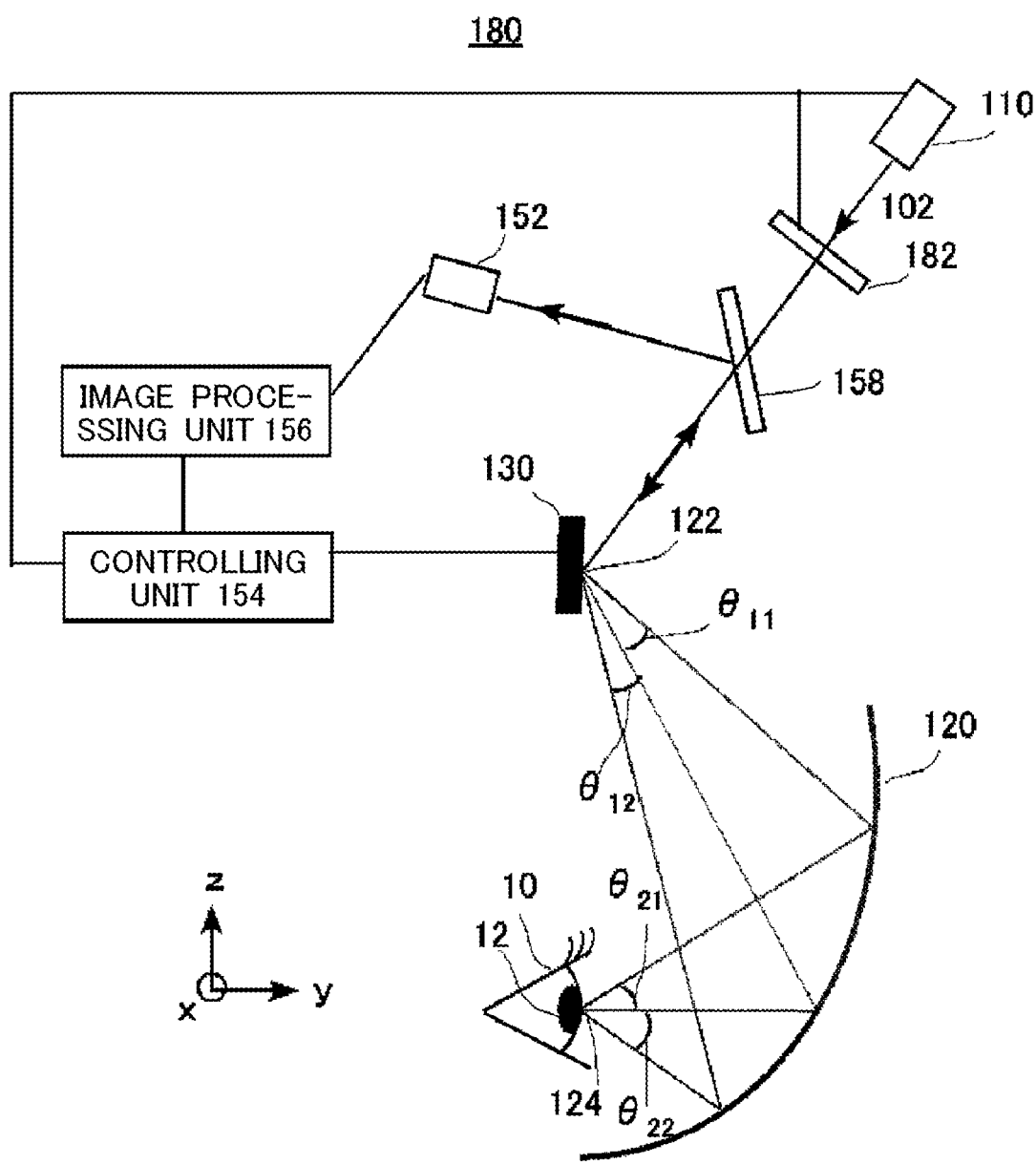
FIG. 4 is a schematic diagram of still another fundus imaging system 180.

FIG. 4 is a schematic diagram of still another fundus imaging system 180. In the fundus imaging system 180, the same configurations as the fundus imaging system 100 in FIG. 1 are given the same reference numbers, and a description about them will be omitted.

The fundus imaging system 180 has an intensity compensation optical system 182 in addition to the respective configurations of the fundus imaging system 100. The intensity compensation optical system 182 is disposed in the optical path of the light beam 102, and between the light source 110 and the half-silvered mirror 158 in the example in FIG. 4.

The intensity compensation optical system 182 is, for example, a transmission type liquid crystal whose transmittance is variable. The intensity compensation optical system 182 changes an intensity of a transmitting light beam 102 over time in synchronization with at least one of a scan timing or a scan amount at which the two-dimensional scanning unit 130 performs scanning under control of the controlling unit 154. In the above-described example of I1>I2, by lowering the transmittance to $1/\alpha$ under control of the controlling unit 154 at a timing at which the light beam of the angle $\theta_{11}$ corresponding to the intensity I1 has been incident on the light beam, and satisfying $I1/\alpha=I2$, the intensity distribution with the above-described unevenness compensated for is realized.

In this way, the intensity compensation optical system 182 of the embodiment represents another example of a method which corrects the unevenness in illumination by actually correcting the intensity of the light beam 102. In accordance with the embodiment, the illuminance ununiformity can be compensated for with simple and convenient configuration. Note that a reflection type liquid crystal may be used instead of the transmission type liquid crystal. In the case of this configuration, because the compensation is attained by the intensity change of the light beam from the light source 110 itself, both the intensity change with respect to the eye of the subject 10, and the intensity change of the reflected light beam which is reflected off the fundus oculi with respect to intensity detector 152 can be corrected.

As described above, the ratio of the angular change of the light beam which is emitted from the first focus 122 to the angular change of the light beam incident on the second focus 124 is not even. Thus, if the two-dimensional scanning unit 130 is scanning the above-described angular changes $\theta_{11}$, $\theta_{12}$ at a constant speed, the speed at which the two-dimensional scanning unit 130 scans the retina of the eye 10 after passing through the second focus 124 is different.

In this case, if the two-dimensional image of the retina is reconfigured assuming that the image processing unit 156 is scanning the retina at a constant speed, a distortion is introduced in the image due to the above-described speed difference (which distortion may be referred to as a scan distortion). Therefore, in the fundus imaging systems 100, 170, and 180, the scan distortion may be compensated for.

The controlling unit 154 compensates for the scan distortion of the light beam 102 by the detector 152 based on at least one of the scan angle or the scan timing at which the two-dimensional scanning unit 130 performs scanning. As described above, if a geometric parameter such as the eccentricity of the reflection mirror 120 and at least one of the scan angle or the scan timing at which the two-dimensional scanning unit 130 performs scanning are known, the speed difference during scanning can be calculated. Therefore, when the image processing unit 156 maps the detection result as a two-dimensional image, the controlling unit 154 compensates for the above-described scan distortion by correcting the position in the two-dimensional image based on the speed difference.

In this case, the controlling unit 154 may calculate the amount of compensation on a case-by-case basis according to the scan angle and the scan timing, or may store a table and the like in a memory of the controlling unit 154 and the like in advance. The table stores an amount of compensation of the scan distortion in association with at least one of the scan angle or the scan timing which have been calculated based on the geometric parameter of the reflection mirror 120. In this case, the memory of the controlling unit 154 functions as a compensation amount storage unit. Instead of this, an amount of compensation corresponding to at least one of the scan angle and the scan timing may be set, so as to scan an index with known shape or pattern such as a test chart, and so that its reconfiguration image can reproduce the known shape or pattern.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10: eye, 12: pupil, 100: fundus imaging system, 102: light beam, 110: light source, 120: reflection mirror, 122: first focus, 124: second focus, 130: two-dimensional scanning unit, 131: body, 132: junction, 133: frame, 134: junction, 135: reflection mirror, 152: detector, 154: controlling unit, 156: image processing unit, 158: half-silvered mirror, 170: fundus imaging system, 172: intensity compensation optical system, 180: fundus imaging system, and 182: intensity compensation optical system

What is claimed is:

1. A fundus imaging system configured to scan a retina of a subject with a light beam, the system comprising:
    a reflection mirror configured to reflect a light beam incident on the reflection mirror after passing through a first focus so as to cause the light beam to pass through a second focus;
    a two-dimensional scanning unit that is disposed at a position that coincides with a position of the first focus of the reflection mirror and configured to reflect a light beam incident on the two-dimensional scanning unit so as to perform scanning with the light beam in two-dimensional directions;
    a detecting unit configured to detect a light beam reflected off the retina; and
    a compensating unit configured to correct a detection result of an intensity of the light beam detected by the detecting unit, based on at least one of a scan angle or a scan timing at which the two-dimensional scanning unit performs scanning, so as to compensate for illuminance non-uniformity of the light beam illuminating the retina, the illuminance non-uniformity resulting from an unevenness of a ratio of an angular change of a light beam emitted from the first focus during scanning of the two-dimensional scanning unit to an angular change of a light beam incident on the second focus after being reflected by the reflection mirror.

2. The fundus imaging system according to claim 1, further comprising a compensation-value storage unit configured to store an amount of compensation of the illuminance non-uniformity in association with the at least one of the scan angle and the scan timing at which the two-dimensional scanning unit performs scanning, wherein
    the compensating unit is configured to correct the detection result with reference to the compensation-value storage unit.

3. The fundus imaging system according to claim 1, further comprising an image processing unit configured to reconfigure an image of the retina, based on the at least one of the scan angle and the scan timing at which the two-dimensional scanning unit performs scanning and the detection result of the detecting unit, wherein
    the compensating unit is configured to compensate for a scan distortion introduced in the image of the retina by correcting a position in the image of the light beam each detection result based on a difference between an angular speed of the light beam emitted from the first focus and an angular speed of the light beam incident on the second focus.

4. A fundus imaging system configured to scan a retina of a subject with a light beam, the system comprising:
    a reflection mirror configured to reflect a light beam incident on the reflection mirror after passing through a first focus so as to cause the light beam to pass through a second focus;
    a two-dimensional scanning unit that is disposed at a position that coincides with a position of the first focus of the reflection mirror and configured to reflect a light beam incident on the two-dimensional scanning unit so as to perform scanning with the light beam in two-dimensional directions; and
    a compensating unit configured to compensate for illuminance non-uniformity of a light beam illuminating the retina, the illuminance non-uniformity resulting from an unevenness of a ratio of an angular change of a light beam emitted from the first focus during scanning of the two-dimensional scanning unit to an angular change of a light beam incident on the second focus after being reflected by the reflection mirror,
    wherein the compensating unit has an optical member that is disposed in an optical path of the light beam and configured to adjust an intensity of the light beam during the scanning of the two-dimensional scanning unit so as to compensate for the illuminance non-uniformity of the light beam illuminating the retina.

5. The fundus imaging system according to claim 4, wherein
    the optical member is configured to compensate for the luminance non-uniformity resulting from the unevenness of said ratio by changing an intensity of an emanating light beam over time in synchronization with at least one of a scan angle or a scan timing at which the two-dimensional scanning unit performs scanning.

6. The fundus imaging system according to claim 4, wherein the two-dimensional scanning unit is configured to scan the optical beam across the optical member, the optical member having a transmittance that is distributed two-dimensionally such that an intensity of the light beam that emanates after being transmitted through the optical member is distributed two-dimensionally so as to compensate for the illuminance non-uniformity resulting from the unevenness of said ratio.

7. The fundus imaging system according to claim 4, wherein the two-dimensional scanning unit is configured to scan the optical beam across the optical member, the optical member having a reflectance that is distributed two-dimensionally such that an intensity of the light beam that emanates after being reflected from the optical member is distributed two-dimensionally so as to compensate for the illuminance non-uniformity resulting from the unevenness of said ratio.

8. The fundus imaging system according to claim 4, further comprising:
- a detecting unit configured to detect a light beam reflected off the retina; and
- an image processing unit configured to reconfigure an image of the retina based on at least one of a scan angle or a scan timing at which the two-dimensional scanning unit performs scanning and a detection result of the detecting unit, wherein
- based on the unevenness, the compensating unit is configured to compensate for a scan distortion introduced in the image of the retina.

* * * * *